United States Patent [19]

Reeves et al.

[11] 4,278,088
[45] Jul. 14, 1981

[54] BAG TAMPON CONTAINING DISCRETE PIECES OF ABSORBENT

[75] Inventors: William G. Reeves, Neenah; Douglas C. Thomas, Appleton, both of Wis.

[73] Assignee: Kimberly-Clark Corporation, Neenah, Wis.

[21] Appl. No.: 87,226

[22] Filed: Oct. 22, 1979

[51] Int. Cl.³ .............................................. A61F 13/20
[52] U.S. Cl. .................................................... 128/270
[58] Field of Search ................................ 128/270, 285

[56] References Cited

U.S. PATENT DOCUMENTS

| 2,267,030 | 12/1941 | Hill | 128/270 X |
| 2,298,424 | 10/1942 | Schreiber | 128/270 |
| 3,523,535 | 8/1970 | Croon et al. | 128/285 |
| 3,610,243 | 10/1971 | Jones, Sr. | 128/285 |
| 3,900,030 | 8/1975 | Bashan | 128/270 |
| 3,902,493 | 9/1975 | Baier | 128/270 |
| 4,104,214 | 8/1978 | Meierhoefer | 128/285 X |
| 4,105,033 | 8/1978 | Chatterjee et al. | 128/285 |

Primary Examiner—John D. Yasko
Attorney, Agent, or Firm—Howard Olevsky; William D. Herrick

[57] ABSTRACT

A bag-type tampon which has as its absorbent component discrete pieces of a rigid compressed dry shape retaining absorbent matt which is loosely dispersed throughout the interior of a fluid-permeable bag. The invention also includes a method for making the tampon.

4 Claims, 4 Drawing Figures

BAG TAMPON CONTAINING DISCRETE PIECES OF ABSORBENT

FIELD OF THE INVENTION

This invention relates to a novel tampon and more particularly to a bag-type tampon having compressed absorbent material loosely dispersed therein.

BACKGROUND OF THE INVENTION

Recently a bag-type tampon has been introduced which has some novel characteristics. This tampon described in U.S. Pat. No. 3,815,601 utilizes a fluid-permeable outerwrap and discrete pieces of a compressible foam dispersed therein.

Additional highly absorbent particulate material is mixed in with the foam pieces in the bag to increase the absorptive capacity of the tampon. This is done because the foam pieces do not retain large amounts of fluid and the flexing of the vaginal walls associated with bodily movement tends to squeeze retained fluid out of the interior of the foam.

Tampons of this type are made by filling the porous bag with the absorbent particles and foam, compressing the bag by inserting the tampon in a conventional telescoping inserter. After vaginal insertion, the tampon resumes its original configuration due to the "springing back" of the compressed foam to its original contours. The bag in its original configuration presses against the vaginal walls to prevent leakage around the tampon edges.

While this particular configuration does tend to prevent leakage it makes "dry removal" difficult. If the tampon is removed before substantial flow the bulk of the tampon causes removal difficulties even with compressibility of the foam. The subject invention provides a bag-type tampon and a method for its assembly which overcomes many of the difficulties encountered with the above-mentioned bag-type tampon by utilizing a different absorbent system, and a different manner of assembly.

Superabsorbents or hydrogels as absorptive materials have also been used for tampons. They may produce discomfort for the tampon wearer however. These materials have a strong affinity for fluid, so strong that they produce a suction phenomenon at the surface of the tampon where it contacts the vaginal walls. Removal of the tampon, therefore, produces a shearing force at the surface interface between the vagina and the bag.

SUMMARY OF THE INVENTION

According to this invention a bag-type tampon having small discrete pieces of a compressed dry shape-retaining absorbent rigid paper-like matt. The pieces are loosely packed within a conventional fluid-permeable bag so that there is a substantial open area within the bag interior. By utilizing an absorbent of this type more fluid is absorbed than is the case with the same volume of foam and separate particulate superabsorbent materials to obtain adequate fluid retention levels is not needed. Difficulties encountered with tampon removal associated with particulate superabsorbents are not encountered.

Also since the dry tampon has compressive set absorbent material, the tampon does not expand after insertion, does not have the bulk associated with the prior art bag tampon. Furthermore, since the bag is only loosely packed, the tampon readily alters its overall configuration in response to force generated during either wet or dry removal.

In addition, since the bag is loose, it conforms to the small crevices or folds of the vagina in response to body movement thereby aiding in intercepting of flow and prevention of premature failure of th tampon.

The absorbent material utilized in the subject invention can be broadly defined as containing as its major component compressible cellulosic fibers. These fibers either alone or in combination with similar cellulosic fibers or other absorbent material must be rendered compressible to a degree such that the sheets formed by compression may be cut by conventional paper cutting apparatus. Compression and compressibility, for purposes of this invention relate specifically to that degree of compression which produces the stiffness required for utilization of paper cutting apparatus. "Paper like" for purposes of this invention refers to the gross physical characteristics of the sheet which allows this type of handling. The absorbent material after compression will be more or less similar to stiff paper or cardboard depending upon its individual composition. The sheet material has the thickness of a paper sheet and is generally compressed to a thickness of 0.5 to 0.1 times the thickness of the uncompressed material depending upon the nature of the starting material. Generally the lower level of compression is better. This level of compression can be accomplished by utilizing compression rollers found in the paper making art.

As mentioned previously the absorbent is primarily cellulosic in nature, although other absorbent materials including short superabsorbent fibers may be incorporated into the blend. Rayon which is cellulosic, may be used as the major component of the absorbent material, but to accomplish dry-setting of rayon, heat must be employed during the compression step.

Generally, any of the commercially available cellulosic-based fiber combinations found in tampons, sanitary napkins and the like can be compressed and utilized as the absorbent material for this invention.

One of the advantages of this tampon is the ease of assembly of its various components. After the cellulosic material has been suitably compressed, it is cut by conventional paper cutting apparatus into small discrete pieces generally being about 1/16" to ½" in length and about 1/16" to ½" in width. The size of these pieces are dependent upon the amount of surface area of absorbent per volume of the tampon with smaller pieces, of course, providing desired greater absorptive surface area. Very small individual pieces, however, may be difficult to handle efficiently depending upon the choice of material. An alternative is to cut the material in strip form with a length of 1" to 3" and a width of about ¼" to ½". The cut pieces or strips may then be placed in the outer wrap or bag and the bag is sealed. When strips are used in this way they are preferably rolled together in a jelly roll configuration by aligning them linearly in a parallel configuration on a light nonwoven moisture permeable cloth which is then rolled loosely and placed in the bag.

Alternatively, the strips may be randomly configured within the bag without prior wrapping. (Rolling of the strips is preferred because it increases the surface area available for absorption).

The bag is sealed and withdrawal string attached by any conventional means such as heat sealing, tieing of the bag with the withdrawal string or adhesive sealing and/or mounting of the string.

The choice of bag material is also conventional and may be identical to the nonwoven material used to make the jelly roll configuration. Any of the fluid permeable covers used for catamenial products may be used for the bag material with the choice of bag determinative of method of attachment of withdrawal string and also influencing the type of sealing. Sealing is currently preferred by tying the string around the bottom of the bag and this method is useful regardless of the choice of bag material.

After the absorbent is sealed within the bag, allowing a suitable space within the bag confines for swelling of the absorbent during absorption and shifting of the swollen material within the bag parameters, it is inserted in an insertion device. Introduction of the tampon into the device is currently performed by pulling through a truncated conical insertion means through the bottom or trailing edge of the outer tube, the string is threaded through the inner tube and the tubes are then mated. Alternatively, the string may be attached to the bottom through the forward end of the device. Due to the deformability without compressibility of the bag contents, loading of the device is easily accomplished. It should be noted, that any conventional inserter can be used to deliver the tampon into the vagina.

FIGS. 1, 2, 3 and 4 are side views partially in cross section

Figure 1:
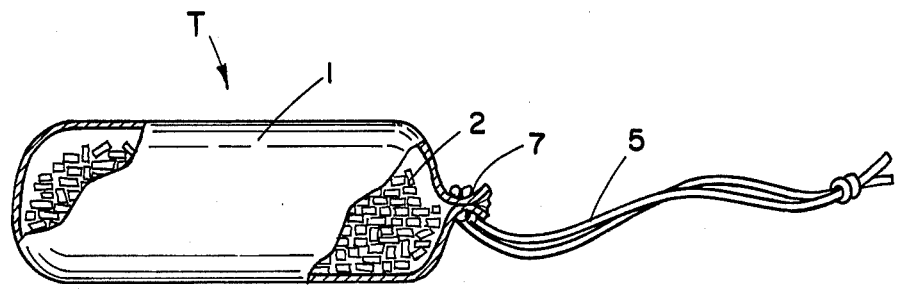
FIGS. 1-4 show the embodiments of the tampon of this invention.
Figure 2:
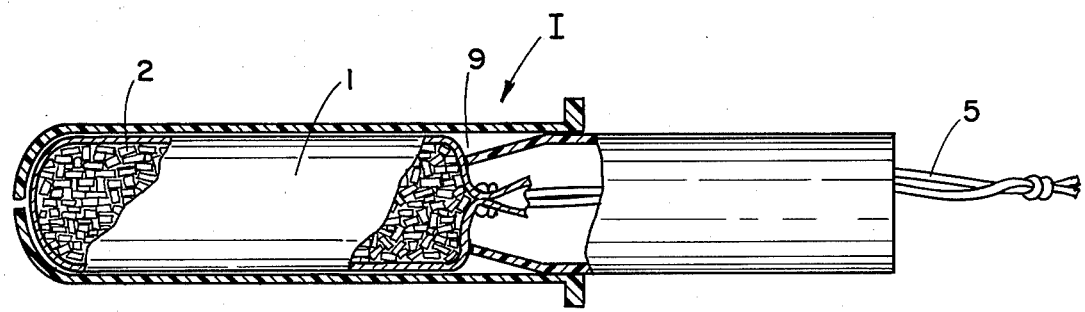

FIG. 1 shows the tampon T with a porous outer wrap 1 enclosing small discrete pieces of compressed absorbent material 2. The bag is closed at the end by withdrawal string 5 which is knotted at the bag end 7.

After the tampon is placed in the inserter I, the tampon T is compressed so that it elongates and conforms to the general configuration of the inside cavity 9 of the delivery portion of the inserter tube.

Figure 3:
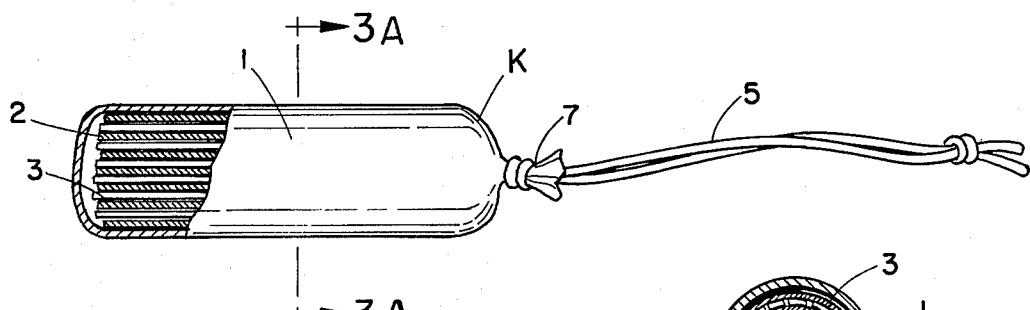
Figure 3A:
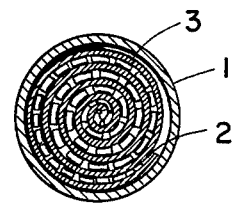
FIG. 3A is a section taken along the lines 3A—3A of FIG. 3.
Figure 4:
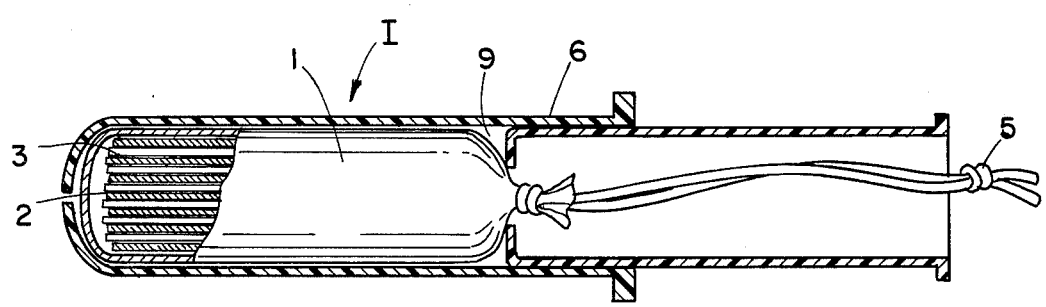

FIGS. 3 and 4 show the jelly roll configuration of the tampon both in and out of the inserter with the moisture permeable wrap 3 surrounding the absorbent strips 2. FIG. 3A shows the jelly roll configuration more graphically from a different cross-sectional view. After insertion of the tampon by the inserter, the tampon conforms generally to the shape of the vaginal opening, but, since there is no release of compression after expulsion by the inserter, the discrete pieces can readily alter their position and hence the dry configuration after insertion.

An Example of the product of this invention follows. This Example illustrates a presently preferred tampon according to the subject invention.

EXAMPLE 1

A matt comprising 60% rayon, 20% cotton linters and 20% AQUALON which is a trademark of the Hercules Company and is a superabsorbent fiber were blended together to form a matt. This matt is typical of absorbent compositions currently used in tampons. The matt was compressed to a thickness half that of the original and cut into $2'' \times \frac{1}{4}''$. Three grams of these pieces were placed on a rayon appliqued nylon scrim which is a nonwoven cloth and parallely aligned so that none are touching and then rolled into a jelly roll configuration and placed into a bag made from a rayon appliqued nylon scrim and tied with a string.

Comparison testing showed that a three gram tampon of the above description was equivalent in absorptive capacity and resistance to premature failure as a four gram tampon made from the same fiber blend but compressed after assembly in the usual fashion.

What is claimed is:

1. A tampon comprising discrete pieces of a compressed, rigid dry-shape retaining absorbent paper-like matt primarily containing cellulosic fibers loosely dispersed in a fluid-permeable bag.

2. The tampon of claim 1 in which the pieces are in the form of curled strips.

3. The tampon of claim 1 in which the strips are not greater than 1.0 inch wide.

4. The tampon of claim 1 in which the absorbent material includes a hydrogel.

* * * * *